United States Patent [19]

Munakata et al.

[11] 4,256,765
[45] Mar. 17, 1981

[54] NOVEL HYDROXAMIC ACID COMPOUNDS, METHOD FOR PREPARATION THEREOF AND MEDICAMENTS CONTAINING SUCH COMPOUNDS

[75] Inventors: Keiichi Munakata, Yono; Satoru Tanaka, Higashi-Kurume; Tamotsu Kanazawa, Tokorozawa; Masaru Satoh, Sayama; Jun-ichi Hase; Kyoichi Kobashi, both of Toyama, all of Japan

[73] Assignee: Eisai Co., Ltd., Tokyo, Japan

[21] Appl. No.: 76,733

[22] Filed: Sep. 18, 1979

[30] Foreign Application Priority Data

Sep. 18, 1978 [JP] Japan ................. 53-113636

[51] Int. Cl.$^3$ ............... C07C 83/10; A61K 31/185
[52] U.S. Cl. ..................... 424/315; 260/500.5 H
[58] Field of Search ............ 260/500.5 H; 424/315

[56] References Cited

U.S. PATENT DOCUMENTS

| | | | |
|---|---|---|---|
| 2,279,560 | 4/1942 | Dietrich | 260/500.5 H |
| 2,279,973 | 4/1942 | Dietrich | 260/500.5 H |
| 3,804,888 | 4/1974 | Johnson et al. | 260/500.5 H |
| 4,157,396 | 6/1979 | Tanaka et al. | 260/500.5 H |

*Primary Examiner*—Joseph E. Evans
*Attorney, Agent, or Firm*—Wenderoth, Lind & Ponack

[57] ABSTRACT

A novel hydroxamic acid compound represented by the general formula:

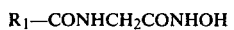

wherein $R_1$ is an alkyl, cycloalkyl or cycloalkyl alkyl group having from 4 to 11 carbon atoms, and pharmacologically acceptable salt thereof, and a method for the preparation of the above-mentioned compound and salt, and a novel medicament for the treatment of urolithiasis and pyelonephritis, containing the above-mentioned compound or salt as an active ingredient.

15 Claims, No Drawings

NOVEL HYDROXAMIC ACID COMPOUNDS, METHOD FOR PREPARATION THEREOF AND MEDICAMENTS CONTAINING SUCH COMPOUNDS

This invention relates to novel hydroxamic acid compounds, method for preparation thereof and medicament containing the same, and more particularly relates to novel hydroxamic acid compounds having the general formula:

$$R_1-CONHCH_2CONHOH \qquad (I)$$

wherein $R_1$ represents an alkyl, cycloalkyl or cycloalkyl alkyl group containing from 4 to 11 carbon atoms, and its pharmacologically acceptable salt, method for preparation thereof and medicament containing said compound and salt as an active ingredient for the treatment of urolithiasis and pyelonephritis due to infection of urease-producing bacterium.

In the general formula (I), the alkyl group containing from 4 to 11 carbon atoms may be any straight, branched or cyclic alkyl, such, for example, as isobutyl, 1-methylpropyl, tert-butyl, n-pentyl, 1-ethylpropyl, isoamyl, n-hexyl, n-heptyl, n-octyl, n-nonyl, n-decyl, n-undecyl, cyclohexyl, cyclohexylmethyl, cyclohexylethyl, adamantyl and the like.

Illustrative of the compounds of this invention are those mentioned as follows:

N-(pivaloyl)-glycinohydroxamic acid

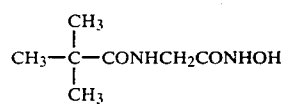

N-(2-ethyl-n-butyloyl)-glycinohydroxamic acid

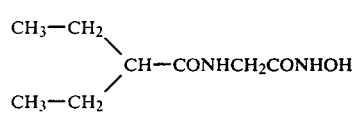

N-(DL-2-methyl-n-butyloyl)-glycinohydroxamic acid

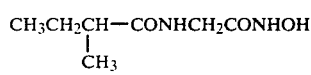

N-(n-decanoyl)-glycinohydroxamic acid $$CH_3(CH_2)_8CONHCH_2CONHOH$$

N-(n-caproyl)-glycinohydroxamic acid $$CH_3(CH_2)_4CONHCH_2CONHOH$$

N-(isovaleryl)-glycinohydroxamic acid

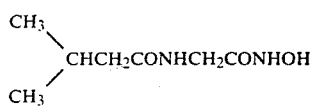

N-(cyclohexylcarbonyl)-glycinohydroxamic acid

N-(α-cyclohexlacetyl)-glycinohydroxamic acid

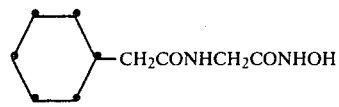

N-(β-cyclohexylpropionyl)-glycinohydroxamic acid

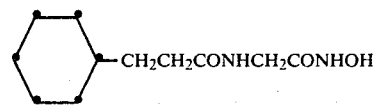

N-(isocaproyl)-glycinohydroxamic acid

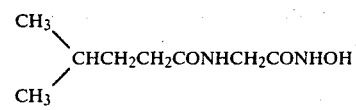

N-(n-dodecanoyl)-glycinohydroxamic acid $$CH_3(CH_2)_{10}-CONHCH_2CONHOH$$

N-(n-nonanoyl)-glycinohydroxamic acid $$CH_3(CH_2)_7CONHCH_2CONHOH$$

N-(n-octanoyl)-glycinohydroxamic acid $$CH_3(CH_2)_6CONHCH_2CONHOH$$

N-(n-heptanoyl)-glycinohydroxamic acid $$CH_3(CH_2)_5CONHCH_2CONHOH$$

Illustrative of the pharmacologically acceptable salts of the compound represented by the general formula (I) are inorganic salts such as the salts of sodium, potassium, magnesium, calcium, aluminium and the like, and organic salts such as the salts of piperidine, morpholine, dimethylamine, diethylamine and the like.

The compound (I) of this invention is usually synthesized according to the following reaction schema:

$$R_1-CONHCH_2COOR_2 + NH_2OH \longrightarrow$$
$$(II)$$
$$R_1-CONHCH_2CONHOH + R_2OH$$
$$(I)$$

wherein $R_1$ represents the same meaning as defined above, and $R_2$ represents a lower alkyl group. This intended compound (I) is obtained by reacting an alkyl ester compound of N-(acyl)-glycine, represented by the formula (II), with hydroxylamine in the presence of an alkali.

This reaction is usually carried out in a reaction solvent of a lower alcohol such as methanol, ethanol, propanol, isopropanol and the like, in a pure state or as a mixture with water. In this reaction system, there is usually present an alkali which can be, for example, sodium hydroxide, potassium hydroxide, sodium carbonate, potassium carbonate, sodium hydrogen carbonate, potassium hydrogen carbonate and the like.

The hydroxamic acid compound (I) and their pharmacologically acceptable salts produced according to this invention are all novel compounds which have not yet been described heretofore in any literatures. They are superior in effect and useful as pharmaceutical compounds for the treatment of urolithiasis.

Urolithiasis is one of the incurable diseases in recent urological fields, which is referred to as a general term for diseases including those of renal pelvis, calix, ureteral, vesical, ureteral, prostatic calculi and the like.

Urolithiasis is classified into a phosphate, an oxalate, a uric acid and a cystine calculus disease and the like. These calculi are often discovered as mixed urinary calculi. The percentage of the phosphate calculus disease including the mixed urinary calculi is estimated to be about 40–60% from various statistical data. Thus, the phosphate calculus disease is one of two typical calculus diseases, together with the oxalate calculus disease.

The phosphate calculus is generally formed according to the following steps:

Urea in urine is decomposed to yield ammonia by a urease-producing bacterium such as *Proteus mirabilis* and the like infecting the urinary tract; urine is alkalized by the said ammonia, resulting in deposition of the calculus as an insoluble phosphate such as magnesium ammonium phosphate and the like. [Refer to H. Takeuchi et al. "Acta Urol. Jap. (in Japanese)" 23 (7), 647–651 (1977).]

The phosphate calculus disease owing to such urinary tract infection is considered as malignant urolithiasis, comparing with other calculus disease.

The typical clinical treatment for the phosphate calculus disease at the present time are the two countermeasures, one of which is to remove the calculus by means of surgical treatment, and the other is to remove the urease-producing bacterium such as *Proteus mirabilis* and the like by means of administration of an antibiotic for the urinary tract system such as Ampicillin and the like. However, surgical treatment has a limitation, because it is difficult to completely remove the phosphate calculus due to its breakable and brittle nature, resulting in that calculus disease often repeatedly recurs. In respect of the medicinal therapy by the antibiotics for the urinary tract system, it is well known to the clinician that the effects of such antibiotics are rapidly decreased. It is considered that one of the factors of such decreased efficacy of antibiotics is due to an insufficient clearance of bacteria, because of the presence of the phosphate calculus.

Furthermore, in view of the matters of emergence of resistant bacteria, superinfection (microbisme selectionné et substitué) and side effects, it is not preferable to administer antibiotics in a large amount or continuously for a long period of time. At the present state, the purpose of treatment of the phosphate calculus disease can not be achieved by a single administration of antibiotics. For such reason, the third method for the treatment of phosphate calculus has been earnestly desired by clinicians.

Recently, there has been attention given to the mechanism mentioned above for forming the phosphate calculus, and hydroxamic acid compounds which specifically inhibit the decomposition of urea in urine into ammonia by urease activity have been. It is generally known that many hydroxamic acid compounds exhibit a specific and potent urease inhibitory activity. [Refer to K. Kobashi et al. "Biochim. Biophys. Acta", 65, 380–383 (1962); "Biochim, Biophys. Acta", 227, 429–441 (1971).] However, many hydroxamic acid compounds are rapidly metabolized in vivo, resulting in that percentages of urinary excretion of hydroxamic acid in an unchanged form, that is, in a form having urease inhibitory activity, are generally very low, with the recovery of approximately one percent. [Refer to H. Takeuchi et al., "Acta Urol. Jap. (in Japanese)" 23, 113–118 (1977); K. Kobashi et al.; "Yakugaku Zasshi" 93, 1564–1572 (1973).] Therefore, such hydroxamic acid compounds are not clinically used.

Griffith et al. reported the preventive effect of alkalization of urine in rats, and the treatment of experimental phosphate calculus disease in rats by acetohydroxamic acid. [Refer to Muscher, D. M., Griffith, D. M., et al. "Clinical Research" 21 (3), 607 (1973).] Griffith et al. further reported their clinical study of urolithiasis by acetohydroxamic acid, wherein the said acid was effective for decreasing the amount of ammonia in urine, and preventing the alkalization of urine. [Refer to Griffith, D. M. et al., "The Journal of Urology", 119, 9–15 (1978).]

It is clinically known that the pyelonephritis due to the infection of urease-producing bacterium such as *Proteus mirabilis* and the like becomes serious, because of the influence of toxicity of ammonia generated from the decomposition of urea in urine. [Refer to Maclaren, D. M., J. Pathol., "Bacteriol" 96, 45 (1968); ibid, 97, 43 (1969); Muscher, D. M., et al., "The Journal of Infectious Disease" 131, (2), 177 (1975).] Maclaren reported the treatment of experimental pyelonephritis in mice by the acetohydroxamic acid. [Refer to Maclaren D. M. "Investigative Urology", 12 (2), 146 (1974).]

Andersen reported the effectiveness of 2-(para-chlorobenzamide)-acetohydroxamic acid ("Benurestat") in an experiment involving phosphate calculus disease in rats. [Refer to Andersen, J. A. "Investigative Urology", 12 (5), 381 (1975).]

However, in our further toxicological study, it was found that said two hydroxamic acid compounds had a serious defect in view of the safety, and accordingly, they are not preferable for the treatment of urolithiasis. That is, it was clarified that these hydroxamic acid compounds had mutagenic activity in microbial tests. This finding indicates the possibility of genetic toxicity and carcinogenicity. It is clinically expected that these kinds of medicaments are administered continuously for a long period of time for the treatment of the urolithiasis of phosphate calculus, because this disease is particularly incurable. Because a relatively large number of the patients belong to the relatively young age group such as 30–40 years old, it is clinically a serious matter to administer continuously for a long period of time such medicament which has a dangerous possibility of genetic toxicity and carcinogenicity due to said mutagenic activity.

We previously sought to find hydroxamic acid compounds having a potent urease inhibitory activity and high renal clearance, and discovered that 2-(para-methoxybenzamide)-acetohydroxamic acid, 2-(metamethoxybenzamide)-acetohydroxamic acid, 2-(2-furoylamino)-acetohydroxamic acid, 2-(meta-acetylaminobenzamide)-acetohydroxamic acid and the like show these two criteria, and are promising medicaments for urolithiasis. (Refer to Japanese patent application Laid-Open No. 100,435/77, Japanese Patent Application Laid-open No. 151,139/77, Japanese Patent Application Laid-open No. 151,158/77 and U.S. Pat. No. 4,083,996.) However, in our further toxicological study it was found that these hydroxamic acid compounds also show mutagenecity and they involve a consideration with regard to safety.

We continued for a long period of time further investigation to find hydroxamic acid compounds having potent urease inhibitory activity, superior renal clearance and no mutagenecity. Finally, we have found the hydroxamic acid compounds represented by the general formula:

$$R_1-CONHCH_2CONHOH \quad (I)$$

wherein $R_1$ is an alkyl, cycloalkyl or cycloalkyl alkyl group having 4–11 carbon atoms and their pharmacologically acceptable salts, which show the criteria mentioned above, resulting in that this invention was accomplished.

The hydroxamic acid compound (I) according to this invention is a medicament for the treatment of urolithiasis, which shows extremely high safety and has a potent urease inhibitory activity, a potent inhibitory activity on calculus formation, high renal clearance, and no mutagenecity, and it may be continuously administerted.

The object of this invention is therefore to provide a novel hydroxamic acid compound which is a very useful pharmaceutical compound for the treatment of urolithiasis and shows high safety.

Another object of this invention is to provide a method for the preparation of a novel hydroxamic acid compound which is very useful as a medicament for the treatment of urolithiasis and has high safety.

A further object of the invention is to provide a medicament for the treatment of urolithiasis and pyelonephritis, containing a novel hydroxamic acid compound.

The effects of this invention are more particularly illustrated by way of the following examples of pharmacological experiments.

The following test compounds are elected among the compounds according to this invention.

TABLE 1

| | Test compounds |
|---|---|
| Compound A | N-(pivaloyl)-glycinohydroxamic acid<br>CH$_3$<br>\|<br>CH$_3$—C—CONHCH$_2$CONHOH<br>\|<br>CH$_3$ |
| Compound B | N-(2-ethyl-n-butyloyl)-glycinohydroxamic acid<br>CH—CONHCH$_2$CONHOH |
| Compound C | N-(DL-2-methyl-n-butyloyl)-glycinohydroxamic acid<br>CH$_3$CH$_2$CH—CONHCH$_2$CONHOH<br>\|<br>CH$_3$ |

[I] Method of the measurement of the urease inhibitory activity and urinary excretion of test compound in rats (1) Measurement of urease inhibitory activity of test compounds Urease was extracted and purified from sword bean and molar concentrations of the test compounds causing 50% inhibition of urease activity ($I_{50}$) were determined by the method of Kobashi et al. [Refer to Biochim, Biophys. Acta 227, 429–441 (1971).]

(2) Measurement of urinary excretion in rats 100 mg/Kg of the test compounds were administered orally to the SD strain male rats weighing about 300 g, and urine specimens excreted within 24 hours were collected by cross-over method. Amounts of the test compounds in urine were determined according to the method of Kobashi et al. [Refer to Yakugaku Zasshi 93 (12), 1564–1572 (1973); J. Biochem. 83, 287–293 (1973).]

(3) Result

The urease inhibitory activity is shown in Table 2.

TABLE 2

| Examination group (one group of 7 rats) | Urease-inhibitory activity $I_{50}$ (M) | Urinary excretion (%) (mean value ± S. E.) |
|---|---|---|
| Compound A | 4.38 × 10$^{-6}$ | 14.6 ± 1.82 |
| Compound B | 0.79 × 10$^{-6}$ | 5.37 ± 0.852 |
| Compound C | 1.29 × 10$^{-6}$ | 9.25 ± 2.16 |

As shown in Table 2, all test compounds have potent urease inhibitory activity. Furthermore, urinary excretion of these compounds are 5–15% and these recovery rates are remarkedly high compared with general hydroxamic acid.

[II] Inhibitory effect of test compound on alkalization of urine and calculus formation (1) Method To 18 ml of normal human urine was added each test compound to make 10$^{-3}$M and 2×10$^{-4}$M test solution in a final concentration.

On the other hand, distilled water was added to 18 ml of normal human urine instead of the test compound to make a blank solution.

To the solution was inoculated intact *Proteus mirabilis* (OM-1) to make a cell suspension of 2.75×10$^5$ cells/ml and harvested at 37° C. Before inoculation and at 8 hours after inoculation, the pH values of the solution were measured.

Inhibitory rate of calculi formation was calculated by measuring the weight of formed calculi.

(2) Results

Table 3 shows results of the determination of inhibitory effect of the test compounds on alkalization of urine.

TABLE 3

| Examination group (one group of 3 rats) | Concentration of the test Compound | pH value (mean value ± S. E.) | |
|---|---|---|---|
| | | Before inoculation | 8 hours after inoculation |
| No addition | 0 | 6.31 ± 0.007 | 8.69 ± 0.007 |
| Compound A | 10$^{-3}$M | 6.37 ± 0.003 | 7.33 ± 0.09 |
| | 2 × 10$^{-4}$M | 6.34 ± 0.007 | 8.41 ± 0.007 |
| Compound B | 10$^{-3}$M | 6.36 ± 0.007 | 6.14 ± 0.01 |
| | 2 × 10$^{-4}$M | 6.32 ± 0.000 | 7.24 ± 0.04 |

Table 4 shows results of measurement of the inhibitory effect of the test compounds on calculus formation in urine.

TABLE 4

| Examination group (one group of 3 rats) | Concentration of the test Compound | Inhibitory rate of calculus formation (%)* (mean value ± S. E.) 8 hours after inoculation |
|---|---|---|
| Compound A | $10^{-3}M$ | 82.0 ± 8.2 |
|  | $2 \times 10^{-4}M$ | 50.0 ± 5.2 |
| Compound B | $10^{-3}M$ | 95.7 ± 0.0 |
|  | $2 \times 10^{-4}M$ | 93.7 ± 1.6 |

*Inhibitory rate of calculus formation (%) = $\dfrac{\text{Weight of the calculus formed in the group containing no test compound} - \text{Weight of the calculus formed in the group containing test compound}}{\text{Weight of the calculus formed in the group containing no test compound}} \times 100$

TABLE 6

| Time after administration (Hours) | Test Compound | Numbers of rats | Protein | | | | Glucose | | | Ketone Body | | | Occult Blood | | | Bilirubin | | | Urobilinogen | | |
|---|---|---|---|---|---|---|---|---|---|---|---|---|---|---|---|---|---|---|---|---|---|
| | | | − | ± | + | ++ | +++ | − | + | ++ | − | + | ++ | − | + | ++ | − | + | ++ | − | ± | ++ |
| 0-6 | None | 5 | 5 | | | | | 5 | | | 5 | | | 5 | | | 5 | | | 5 | | |
| | Compound A | 5 | 5 | | | | | 5 | | | 5 | | | 5 | | | 5 | | | 5 | | |
| | Compound B | 5 | 5 | | | | | 5 | | | 5 | | | 5 | | | 5 | | | 5 | | |
| 6-24 | None | 5 | 5 | | | | | 5 | | | 5 | | | 5 | | | 5 | | | 5 | | |
| | Compound A | 5 | 5 | | | | | 5 | | | 5 | | | 5 | | | 5 | | | 5 | | |
| | Compound B | 5 | 1 | 4 | | | | 5 | | | 5 | | | 5 | | | 5 | | | 5 | | |

As obvious in Tables 3 and 4, Compounds A and B inhibited the alkalization of urine and the calculus formation in urine caused by *Proteus mirabilis* (OM-1) inoculated to normal human urine specimens.

[III] Acute toxicity (LD$_{50}$)
(1) Method
The test compounds were administered orally to SD strain male rats weighing about 270 g and SD strain female rats weighing about 170 g.
(2) Result
The results of the measurement are shown in Table 5.

TABLE 5

| Examination group (one group of 8 rats in both male and female groups) | LD$_{50}$ mg/Kg |
|---|---|
| Compound A | >9,000 |
| Compound B | >9,000 |
| Compound C | >9,000 |

As obvious from Table 5, it was affirmed that the acute toxicities of the Compounds A, B and C are all low and they have high safety.

[IV] Acute toxicity (Examination of urine)
(1) Method

To SD strain female rats weighing about 200 g, 1000 mg/Kg of the test compounds were orally administered. Urine specimens excreted within 0-6 hours and 6-24 hours, respectively, after the oral administration were collected and examined.
(i) Protein, glucose, ketone body and occult blood in urine were measured by the reaction using Labstix test paper (manufactured and sold by Miles Sankyo Company in Japan).
(ii) Bilirubin was measured by using Ictostix test paper (manufactured and sold by Miles Sankyo Company in Japan).
(iii) Urobilinogen was measured by Urobilistix test paper (manufactured and sold by Miles Sankyo Company in Japan).
(2) Result
The results of measurement are shown in Table 6.

As obvious from Table 6, examination of urine did not show any abnormalities caused by Compounds A and B, and kidney toxicity was not observed. Therefore, it is recognized that these compounds according to this invention also have high safety from this point of view.

[V] Mutation test
(1) Method
The screening of mutagenicity was carried out according to Ames test [Refer to Ames B. N. et al.: Proc: Natl. Acad. Sci. U.S.A., 72, 979-983 (1975)] which is now widely utilized all over the world as an examination for detection of mutagenicity.
Using the strain of *Salmonela typhimurium* TA-98 and TA-100 as the test bacteria, the mutageic activity was examined for the test compounds untreated with S-9 (9,000×g supernatant fraction of the rat liver homogenate induced with PCB) and the test compounds treated with S-9, respectively. The examined concentration of the test compounds was up to 40,000 μg/ml. Dimethyl sulfoxide (DMSO) was used as solvent.
The result of examination was judged to be positive, when the number of reverse mutation colony was twice comparing with the control group and the positive correlation between dosage and mutagenic activity of the test compound was recognized.
(2) Result
Table 7 shows the results.

TABLE 7

| Test Compound | Salmonella typhimurium TA - 98 | | Salmonella typhimurium TA - 100 | |
|---|---|---|---|---|
| | No addition of S-9 | Addition of S-9 | No addition of S-9 | Addition of S-9 |
| Compound A | — | — | — | — |
| Compound B | — | — | — | — |

TABLE 7-continued

| Test Compound | Salmonella typhimurium TA - 98 | | Salmonella typhimurium TA - 100 | |
|---|---|---|---|---|
| | No addition of S-9 | Addition of S-9 | No addition of S-9 | Addition of S-9 |
| Compound C | − | − | − | − |
| $CH_3(CH_2)_6CONHCH_2CONHOH$ | − | − | − | − |
| $CH_3(CH_2)_7CONHCH_2CONHOH$ | − | − | − | − |
| $CH_3(CH_2)_8CONHCH_2CONHOH$ | − | − | − | − |
| $CH_3(CH_2)_{10}CONHCH_2CONHOH$ | − | − | − | − |
| $\begin{array}{c}CH_3\\ \phantom{x}\diagdown\\ \phantom{xx}CHCH_2CONHCH_2CONHOH\\ \phantom{x}\diagup\\ CH_3\end{array}$ | − | − | − | − |
| 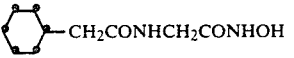—$CH_2CONHCH_2CONHOH$ | − | − | − | − |
| —$CH_2CH_2CONHCH_2CONHOH$ | − | − | − | − |
| $CH_3O$——$CONHCH_2CONHOH$ | + | + | + | + |
| —$CONHCH_2CONHOH$ ($CH_3O$) | + | + | + | + |
| —$CONHCH_2CONHOH$ ($NHCOCH_3$) | + | + | + | + |
| (furan)—$CONHCH_2CONHOH$ | + | + | + | + |
| $Cl$—(phenyl)—$CONHCH_2CONHOH$* | + | + | + | + |
| $CH_3CONHOH$** | + | + | + | + |

In Table 7, (+) represents "positive", and (−) represents "negative" in the mutagenic activity test.
*Benurestat
**Acetohydroxamic acid As clear from Table 7, the mutagenic activity was not observed in the compounds according to this invention. The mutagenic activity was observed in all control compounds, and therefore it is fearful that the control compounds may have a possibility of genetic toxicity and carcinogenicity.

In view of the results of the above pharmacological experiments, it was clarified that the compounds according to this invention have potent urease inhibitory activity and remarkable urinary excretion as high as 5–15% and therefore have an excellent inhibitory effect on the calculus formation. Further, it is very important that the compounds according to this invention have no mutagenic activity and therefore have great safety, contrary to the fact that many known hydroxamic acid compounds such as acetohydroxamic acid, Benurestat [2-p-chloro-benzamide-acetohydroxamic acid] and the like which are shown in Table 7 have the mutagenic activity. Since urolithiasis is an incurable disease, it is necessary to administer the medicaments continuously for a long period of time. Furthermore, in consideration of the case that they are administered to comparatively young patients such as those 30–40 years old, the above-mentioned point is very important. With reference to the fact that all known hydroxamic acid compounds such as acetohydroxamic acid, Benurstat and the like as indicated in Table 7 have mutagenic activity, there is conceived a very great problem in safety on clinic application, when these known hydroxamic acid compounds are administered for a long period of time as medicaments.

On the other hand, since the compounds according to this invention have no such mutagenic activity, they are very valuable in a clinical point of view, as the medicaments for treating urolithiasis. Although the compounds according to this invention may be used in a single form, they may be employed of course in a combination form together with other antibiotics for the urinary tract system such, for example, as Ampicillin, sulfamethoxazole, sulphinemezol, sulfamethopyradine, nitrofurantoin and the like.

Furthermore, it has been said that the pyelonephritis due to the infection of the urease-producing bacterium such as Proteus mirabilis and like becomes serious, because of influence of toxicity of ammonis which is produced by decomposition of urea in urine. The compounds according to this invention are also useful as the medicaments for the treatment of this kind of pyelonephritis. In this case, they may be similarly used together with aforementioned antibiotics for the urinary tract system.

When the compounds according to this invention are used as the medicaments for the treatment of urolithiasis and the pyelonephritis, they are administered orally or parenterally by means of intramuscular injection, subcutaneous injection, intravenous injection, suppository and the like, for example. Although the administration dosage of these compounds are varied depending on the symptoms of disease, the dosage of 20-3,000 mg, preferably 500-1,500 mg per day may generally be administered to an adult patient.

In case of formulating the compounds according to this invention, the compounds may be prepared in various types of formulation such as tablet, granule, powder, capsule, injection, suppository and the like, by conventional methods employed in the technical field of the formulation.

Namely, in case of the production of solid type of oral formulation, the formulation is prepared by adding to the subject active compound, excipients and, if necessary, binders, disintegrators, lubricant, colorant, taste and odor correctives, and casting into tablet, coated tablet, granule, powder, capsule and the like by a conventional manner.

Illustrative excipients which may be employed include lactose, corn starch, white sugar, glucose, sorbit, crystalline cellulose and the like.

There may be mentioned, as binders, polyvinyl alcohol, polyvinyl ether, ethylcellulose, methylcellulose, gum arabic, tragacanth gum, gelatine shellac, hydroxypropyl cellulose, hydroxypropyl starch, polyvinyl pyrolidone, white sugar, sorbit and the like.

Disintegrators includes starch, agar-agar, gelatin powder, crystalline cellulose, calcium carbonate, sodium hydrogen carbonate, calcium succinate, dextrin, pectin and the like.

Illustrative lubricants include magnesium stearate, talc, polyethylene glycol, silica, hardening vegetable oil and the like.

There may be mentioned, as colorant, the materials which are acceptable to add to the medicine.

Taste and odor correctives include cocoa powder, menthol, aromatic powder, peppermint oil, borneol, cinnamon powder and the like.

These tablets and granules may be of course properly coated, if necessary, by way of sugar coating, gelatin coating and the like.

In case of the preparation of liquid formulation for oral administration, the formulation may be prepared by adding to the subject active compounds the taste and odor correctives, buffer, stabilizer and the like, if necessary, and making into administration form of syrup and the like by a conventional way.

In case of the preparation of injection, the formulation may be prepared by adding, to the subject active compound, pH regulator, buffer, suspension agent, solubilizer assistant, stabilizer, isotonizer, antiseptics and the like, if necessary, and filling the resulting solution in an ampoule to obtain subcutaneous intramuscular and intravenous injections by a conventional way.

Illustrative suspension agents which may be employed include methylcellulose, polysorbate 80, hydroxyethyl cellulose, gum arabic, tragacanth powder, sodium carboxymethyl cellulose, polyoxyethylenesorbitane monolaurate and the like.

There may be mentioned, as solubilizer assistant, polyoxyethylene hardened castor oil, polysorbate 80, nicotinic acid amide, polyoxyethylenesorbitane monolaurate, magllogol, castor oil fatty acid ethylester and the like.

Illustrative stabilizers include sodium sulphite, methasodium sulphite, ether and the like.

There may be mentioned, as antiseptics, methyl paraoxybenzoate, ethyl para-oxybenzoate, sorbic acid, phenol, cresol, chlorocresol and the like.

This invention will be illustrated more particularly by the following examples, but this invention is of course not limited only to these examples.

EXAMPLE 1

Synthesis of N-(pivaloyl)-glycinohydroxamic acid 196.8 g (3 M) of potassium hydroxide (85.5%) were dissolved in 600 ml of methanol under cooling. On the other hand, 111.2 g (1.6 M) of hydroxylamine hydrochloride were dissolved in 600 ml of methanol under heating. Both solutions were mixed with each other under a cool condition. Removing the resulting potassium chloride, there was prepared an alkaline methanol solution of hydroxylamine. To the solution were added 224.6 g (1.2 M) of N-(pivaloyl)-glycine ethylester, and the whole was reacted while stirring for 2 hours at a room temperature, and was allowed to stand overnight. Then, the reaction solution was heated to 60° C. under a reduced pressure to distill off the solvent. The residue was dissolved in 800 ml of water, and acetic acid was added to the said solution under cooling and stirring, so that pH of the solution may reach to 5.0 by neutralization. The crystalline masses were filtered, and they were recrystallized from the mixed solution of ethanol and water (3:1), to obtain the objective compound of N-(pivaloyl)-glycinohydroxamic acid which had the melting point (decomposition point) of 170°-171° C. The weight of the product was 174 g (yield 83.3%).

Elemental analysis of the product for $C_7H_{14}O_3N_2$ gives:

|  | C | H | N |
| --- | --- | --- | --- |
| Calculated (%) | 48.26 | 8.10 | 16.08 |
| Found (%) | 48.27 | 8.37 | 16.17 |

EXAMPLE 2

Synthesis of N-(2-ethyl-n-butyloyl)-glycinohydroxamic acid 147.6 g (2.25 M) of potassium hydroxide (85.5%) were dissolved in 600 ml of methanol under cooling. On the other hand, 83.4 g (1.2 M) of hydroxylamine hydrochloride were dissolved in 600 ml of methanol under heating. Both solutions were mixed with each other under a cool condition. Removing the resulting potassium chloride, there was prepared an alkaline methanol solution of hydroxylamine solution. To the solution were added 181.2 g (0.9 M) of N-(2-ethyl-n-butyloyl)-glycine ethylester, and the whole was reacted while stirring for 2 hours at a room temperature, and was allowed to stand overnight. Then, the reaction solution was heated to 60° C. under a reduced pressure to distill off the solvent. The residue was dissolved in 800 ml of water, and acetic acid was added to the said solution under cooling and stirring, so that pH of the solution may reach to 5.0 by neutralization. The crystals produced were filtered and recrystallized from the mixed solution which comprises ethanol and water (3:1), to obtain the objective compound of N-(2-ethyl-n-butyloyl)-glycinohydroxamic acid which had the melting point (decomposition point) of 181°-183° C. The weight of the product was 129 g (yield 76.3%).

Elemental analysis of the product for $C_8H_{16}O_3N_2$ gives:

|  | C | H | N |
|---|---|---|---|
| Calculated (%) | 51.05 | 8.57 | 14.88 |
| Found (%) | 50.97 | 8.77 | 15.02 |

EXAMPLES 3-15

The following Table 8 shows the compounds which are produced in the same manner as in the method of Example 1 or 2.

TABLE 8

$R_1-CONHCH_2CONHOH$

| Ex. | $R_1$ | Melting Point (°C.) | Molecular Formula | Values of Elemental Analysis (%) (Upper Row: Calculated Under Row: Found) | | | Solvent for recrystallization |
|---|---|---|---|---|---|---|---|
|  |  |  |  | C | H | N |  |
| 3 | $CH_3(CH_2)_{10}-$ | 132-133* | $C_{14}H_{28}O_3N_2$ | 61.73 61.84 | 10.36 10.34 | 10.28 10.41 | Methanol/Water |
| 4 | $CH_3(CH_2)_8-$ | 130-131* | $C_{12}H_{24}O_3N_2$ | 58.99 58.68 | 9.90 9.90 | 11.47 11.32 | Ethanol/Water |
| 5 | $CH_3(CH_2)_7-$ | 128-129 | $C_{11}H_{22}O_3N_2$ | 57.36 57.21 | 9.63 9.63 | 12.17 12.13 | Methanol |
| 6 | $CH_3(CH_2)_6-$ | 132-133* | $C_{10}H_{20}O_3N_2$ | 55.53 55.55 | 9.32 9.56 | 12.95 12.89 | Methanol |
| 7 | $CH_3(CH_2)_5-$ | 132-133 | $C_9H_{18}O_3N_2$ | 53.44 53.41 | 8.97 8.94 | 13.85 13.81 | Water |
| 8 | $CH_3(CH_2)_4-$ | 130-131 | $C_8H_{16}O_3N_2$ | 51.05 51.41 | 8.57 8.59 | 14.88 14.82 | Methanol/Water |
| 9 | DL-$CH_3CH_2-CH(CH_3)-$ | 153-154* | $C_7H_{14}O_3N_2$ | 48.26 48.26 | 8.10 7.86 | 16.08 16.09 | Ethanol |
| 10 | $(CH_3)_2CHCH_2-$ | 146-148 | $C_7H_{14}O_3N_2$ | 48.26 48.25 | 8.10 8.18 | 16.08 16.03 | Ethanol/Water |
| 11 | $(CH_3)_2CHCH_2CH_2-$ | 129-130 | $C_8H_{16}O_3N_2$ | 51.05 51.02 | 8.57 8.83 | 14.88 14.95 | Methanol/Ethanol |
| 12 | adamantyl | 154-155 | $C_{13}H_{20}O_3N_2$ | 61.88 61.86 | 7.99 8.18 | 11.10 10.99 | Methanol |
| 13 | $C_6H_{11}-CH_2CH_2-$ | 149-150* | $C_{11}H_{20}O_3N_2$ | 57.87 57.92 | 8.83 8.60 | 12.27 12.26 | Methanol |
| 14 | $C_6H_{11}-CH_2-$ | 155-156* | $C_{10}H_{18}O_3N_2$ | 56.05 56.42 | 8.47 8.28 | 13.08 13.03 | Methanol |
| 15 | $C_6H_{11}-$ | 159-160* | $C_9H_{16}O_3N_2$ | 53.98 53.71 | 8.06 7.97 | 13.99 13.89 | Ethanol |

*Decomposition Point

The following are preparation examples according to this invention.

Preparation example 1: Tablet

| | |
|---|---|
| N-(pivaloyl)-glycinohydroxamic acid | 100g |
| corn starch | 10g |
| lactose | 20g |
| calcium carboxymethylcellulose | 10g |
| microcrystalline cellulose | 45g |
| polyvinyl pyrrolidone | 5g |
| talc | 10g |

Using the above formulation, there were obtained, by conventional process, tablets, each weighing 200 mg.

Preparation example 2: Capsule

| | |
|---|---|
| N-(2-ethyl-n-butyloyl)-glycinohydroxamic acid | 100g |
| lactose | 100g |

Using the above formulation, 200 mg per capsule were filled in hard capsules by a conventional process.

What is claimed is:

1. A hydroxamic acid compound represented by the formula:

$$R_1-CONHCH_2CONHOH$$

wherein $R_1$ is alkyl having from 4 to 11 carbon atoms, cycloalkyl having from 4 to 11 carbon atoms or cycloalkyl alkyl having from 4 to 11 carbon atoms, or a pharmacologically acceptable salt of said compound.

2. The hydroxamic acid compound according to claim 1, wherein the compound is represented by the formula:

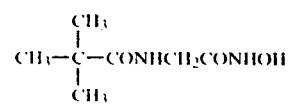

or its pharmacologically acceptable salt.

3. The hydroxamic acid compound according to claim 1, wherein the compound is represented by the formula:

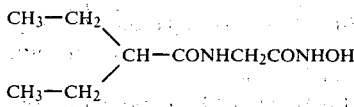

or its pharmacologically acceptable salt.

4. The hydroxamic acid compound according to claim 1, wherein the compound is represented by the formula:

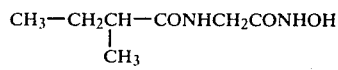

or its pharmacologically acceptable salt.

5. The hydroxamic acid compound according to claim 1, wherein the compound is represented by the formula:

$CH_3(CH_2)_{10}$—CONHCH$_2$CONHOH or its pharmacologically acceptable salt.

6. The hydroxamic acid compound according to claim 1, wherein the compound is represented by the formula:

$CH_3(CH_2)_8$—CONHCH$_2$CONHOH or its pharmacologically acceptable salt.

7. The hydroxamic acid compound according to claim 1, wherein the compound is represented by the formula:

$CH_3(CH_2)_7$—CONHCH$_2$CONHOH or its pharmacologically acceptable salt.

8. The hydroxamic acid compound according to claim 1, wherein the compound is represented by the formula:

$CH_3(CH_2)_6$—CONHCH$_2$CONHOH or its pharmacologically acceptable salt.

9. The hydroxamic acid compound according to claim 1, wherein the compound is represented by the formula:

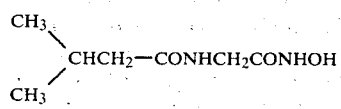

or its pharmacologically acceptable salt.

10. The hydroxamic acid compound according to claim 1, wherein the compound is represented by the formula:

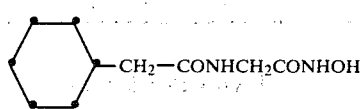

or its pharmacologically acceptable salt.

11. The hydroxamic acid compound according to claim 1, wherein the compound is represented by the formula:

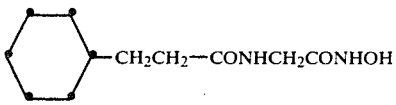

or its pharmacologically acceptable salt.

12. A phrmaceutical composition useful for the treatment of urolithiasis or pyelonephritis due to infection of urease-producing bacterium, which comprises
as an active ingredient, a hydroxamic acid compound represented by the formula:

$R_1$—CONHCH$_2$CONHOH wherein $R_1$ is alkyl having from 4 to 11 carbon atoms, cycloalkyl having from 4 to 11 carbon atoms or cycloalkyl alkyl having from 4 to 11 carbon atoms, or a pharmacologically acceptable salt of said compound, and
a pharmaceutically acceptable carrier therefor.

13. The composition according to claim 12, wherein the active principle is the hydroxamic acid compound represented by the formula:

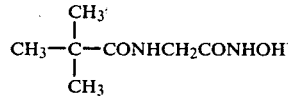

or its pharmacologically acceptable salt.

14. The composition according to claim 12, wherein the active ingredient is the hydroxamic acid compound represented by the formula:

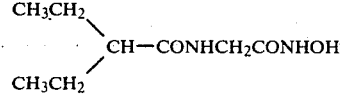

or its pharmacologically acceptable salt.

15. The composition according to claim 12, wherein the active ingredient is the hydroxamic acid compound represented by the formula:

$CH_3(CH_2)_6$CONHCH$_2$CONHOH or its pharmacologically acceptable salt.

* * * * *